Figure 1:
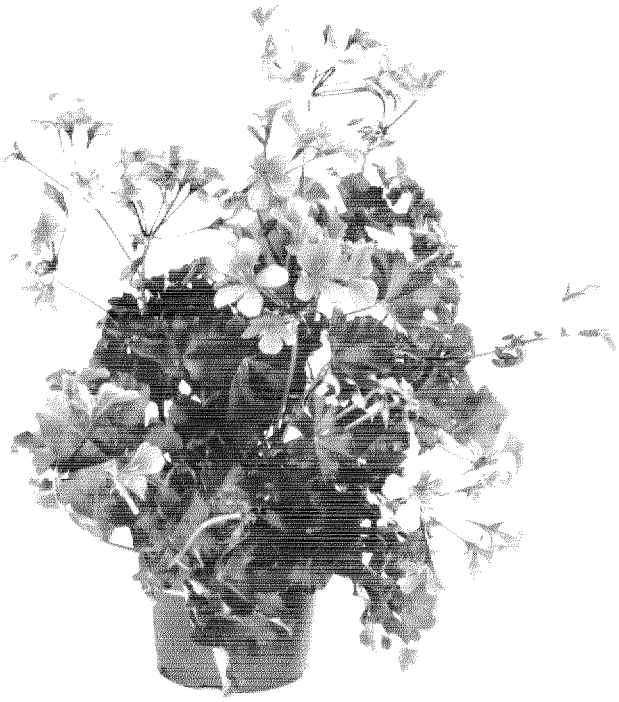

US00PP10814P

United States Patent [19]

Guillou

[11] Patent Number: Plant 10,814

[45] Date of Patent: Mar. 2, 1999

[54] GERANIUM PLANT NAMED 'GUICOR'

[75] Inventor: Bernard Guillou, Saint-Malo, France

[73] Assignee: ETS. Guillou Freres, Saint-Malo, France

[21] Appl. No.: 592,239

[22] Filed: Jan. 26, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named 'Guicor,' characterized by its pink-red single type flowers that are large and that have petals which do not overlap; a bushy plant habit that produces many branches and medium-green foliage with leaves that lack, or have very weak, zonation.

3 Drawing Sheets

1

The present invention comprises a new and distinct cultivar of geranium, botanically known as *Pelargonium peltatum*, and hereinafter referred to by the cultivar name 'Guicor'.

'Guicor' is a product of a planned breeding program which had the objective of creating new geranium cultivars with pink single flowers with red buds and a very weak zonation on the leaves.

'Guicor' was originated from a hybridization made by inventor Bernard Guillou in a controlled breeding program in Saint Malo, Bretagne, France, in 1989. The female and male parents were unnamed hybrids from the proprietary Guillou collection, both parents being characterized by single pink and red flowers, neither parent had a compact plant habit.

'Guicor' was discovered and selected as one flowering plant within the progeny of the stated cross by the inventors in 1989 in a controlled environment in Saint Malo, Bretagne, France.

The first act of asexual reproduction of 'Guicor' was accomplished when vegetative cuttings were taken from the initial selection in 1989 in a controlled environment in Saint-Malo, Bretagne, France by a technician working under the supervision of the inventor.

Horticultural examination of selected units initiated in Hannover, Germany, has demonstrated that the combination of characteristics as herein disclosed for 'Guicor' are firmly fixed and are retained through successive generations of asexual reproduction.

'Guicor' has not been observed under all possible environmental conditions. The phenotype may vary with variations in environment such as temperature, light intensity and day length without a change in the genotype of the cultivar. The following observations, measurements, and comparisions describe plants grown in Hannover, Germany under greenhouse conditions which approximate those generally used in commercial practice.

The following traits have been repeatedly observed and are determined to be basic characteristics of 'Guicor', which in combination, distinguish this geranium as a new and distinct cultivar:

1. Pink-red single-type and large flowers.
2. Red buds.
3. Bushy plant habit.
4. Medium green foliage with an absent or very weak zonation.
5. Well branched plant habit.

There is no cultivar which can be closely compared to 'Guicor'. Among red geranium, the cultivar Renee U.S. Plant Pat. No. 7,353 has a similar plant habit as 'Guicor'.

2

Figure 2:
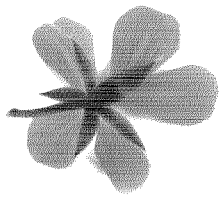
Figure 3:
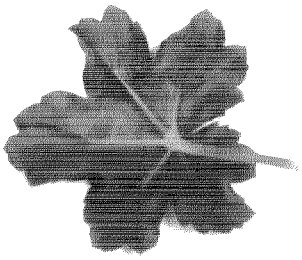

The accompanying color photographs show typical flower and foliage characteristics of 'Guicor', with colors being as true as possible with photographs of this type. FIG. 1 is a side view of the cultivar. FIG. 2 is the top side view of a typical leaf and flower from 'Guicor'. FIG. 3 is a bottom side view of a typical leaf and flower from 'Guicor'.

In the following description, color references are made to The Royal Horticultural Society (R.H.S.) Colour Chart. The color values were determined in 1994 under greenhouse conditions in Hannover, Germany.

Classification:

*Botanical.*—A hybrid of the species *Pelargonium peltatum.*

*Commercial.*—Ivy geranium, cultivar 'Guicor'.

Inflorescence

Umbel:

*Average diameter.*—Approximately 100 mm.

*Average depth.*—Approximately 60–70 mm.

*Peduncle length.*—Approximately 140–150 mm.

*Pedicel length.*—Approximately 40 mm.

Corolla:

*Average diameter.*—Approximately 50 mm.

*Form.*—Single-type with no overlapping of petals; each corolla has five petals.

*Color (general tonality from a distance of three meters).*—Pink.

*Color (petal tips).*—Purple-red, approximately R.H.S. 57 C.

*Color (petal center).*—Pink-red, approximately R.H.S. 52 B.

Bud:

*Markings.*—Dark veins at base of upper petals.

*Shape.*—Asymmetric.

*Color (immature).*—Green.

*Color (mature).*—Red.

Reproductive organs:

*Androecium.*—3–7 fertile anthers; white filaments, orange pollen.

*Gynoecium.*—5–6 lobed stigma, red style and stigma.

Spring flowering response period: 15 weeks after planting unrooted cuttings 1 to 6 open umbels are produced (pinched plants); the number of flowers per umbel does not vary with age, season or plant vigor; the plant does not stop flowering at seed set; the plant does not have to be pinched to induce further flower bud formation.

Outdoor flower production: 80–90 umbels per plant from April–May throughout September–October.
Durability: Shatter resistance is good.

Plant

Foliage:
*Form.*—Ivy-shaped diameter of 5 to 7 cm.
*Margin.*—Approximately 7 indentations per leaf base with no variegation.
*Color (abaxial).*—Medium-green, approximately R.H.S. 137C.
*Color (adaxial).*—Medium-green.
*Color of zonation.*—Green, absent to very weak.
*Tolerance of botrytis.*—Good.
General appearance and form:
*Internode length.*—30–40 mm.
*Branching pattern.*—5–6 branches per plant.
*Height.*—70 cm. in August.

I claim:

1. A new distinct cultivar of geranium plant named 'Guicor,' as illustrated and described.

* * * * *